(12) United States Patent
Berrens et al.

(10) Patent No.: US 6,660,495 B2
(45) Date of Patent: Dec. 9, 2003

(54) TOLEROGENIC FRAGMENTS OF NATURAL ALLERGENS

(75) Inventors: Lubertus Berrens, Utrecht (NL); Maria Leticia Gonzales Romano, Tres Cantos (ES); Maria Teresa Gallego Camara, Tres Cantos (ES)

(73) Assignee: C.B.F. Leti, S.A., Tres Cantos (ES)

( * ) Notice: Subject to any disclaimer, the term of this patent is extended or adjusted under 35 U.S.C. 154(b) by 0 days.

(21) Appl. No.: 10/000,453

(22) Filed: Dec. 4, 2001

(65) Prior Publication Data

US 2002/0086348 A1 Jul. 4, 2002

Related U.S. Application Data

(62) Division of application No. 09/530,277, filed as application No. PCT/NL97/00598 on Oct. 30, 1997, now Pat. No. 6,350,590.

(51) Int. Cl.[7] ............................ C12P 21/06; C12N 9/50; A61K 35/78
(52) U.S. Cl. ...................... 435/68.1; 435/219; 530/370; 530/372; 530/379; 530/412; 530/416; 530/417; 530/427
(58) Field of Search ................................. 530/370, 372, 530/379, 412, 416, 417, 427; 435/68.1, 219

(56) References Cited

U.S. PATENT DOCUMENTS 5,770,698 A    6/1998  Berrens
6,190,723 B1 * 2/2001  Buchanan et al. .......... 530/403
6,201,110 B1 * 3/2001  Olsen et al. ................. 530/403
6,350,590 B1 * 2/2002  Berrens et al. ............. 435/68.1

FOREIGN PATENT DOCUMENTS

WO    WO 94 06821    3/1994

OTHER PUBLICATIONS

Gonzalez Romano et al., "Extraordinary stability of IgE-binding Parietaria pollen allergens in relation to chemically bound flavonoids,", Mol. Immunology, 1997, volume date 1996, 33(17/18), 1287–1293.

Berrens et al., "Haemolytic complement consumption by Parietaria pollen extracts in relation to peptide-bound flavonoids", CMLS Cellular and Molecular Life Sciences, 53(3), 1997, 275–278.

* cited by examiner

Primary Examiner—Herbert J. Lilling
(74) Attorney, Agent, or Firm—Browdy and Neimark, P.L.L.C.

(57) ABSTRACT

The present invention relates to a process for the controlled enzymatic cleavage of purified and depigmented active allergenic proteins from indoor and outdoor source materials, which process produces fragments of allergens that retain the natural T-lymphocyte stimulating epitopes, but are depleted of IgE-binding B-cell epitopes and complement-activating agents. The invention also relates to the new pharmaceutical products. These allergen fragments do not exhibit the disadvantages of conventional allergenic extracts for immunotherapy and can be safely used to induce a state of specific T-cell anergy and immunological tolerance in allergic human beings.

1 Claim, 3 Drawing Sheets

TOLEROGENIC FRAGMENTS OF NATURAL ALLERGENS

RELATED APPLICATIONS

The present application is a division of U.S. application Ser. No. 09/530,277 filed Jun. 23, 2000 now U.S. Pat. No. 6,350,590 which is the national stage under 35 USC §371 of International application PCT/NL97/00598 which designated the United States, has an international filing date of Oct. 30, 1997, and was published under PCT article 21(2) in English.

SUMMARY OF THE INVENTION

The present invention relates to a process for the controlled enzymatic cleavage of purified and depigmented active allergenic proteins from indoor and outdoor source materials, which process produces fragments of allergens that retain the natural T-lymphocyte stimulating epitopes, but are depleted of IgE-binding B-cell epitopes and complement-activating agents. The invention also relates to the new pharmaceutical products. These allergen fragments do not exhibit the disadvantages of conventional allergenic extracts for immunotherapy and can be safely used to induce a state of specific T-cell anergy and immunological tolerance in allergic human beings.

GENERAL BACKGROUND

Aqueous extracts of various environmental substrates, like house dust, the shed epithelial debris of animal skins, the pollen grains of grasses, weeds, trees, and several other materials are widely used for the in vivo and in vitro diagnosis of allergic diseases like bronchial asthma, vasomotor rhinitis and pollinosis in predisposed human, so-called "atopic" patients. Since the first clinical reports by Noon and Freeman in 1911, such extracts have also been applied for the treatment of atopic allergic diseases in a regimen of subcutaneous injections for the "desensitization", "hyposensitization", or "immunotherapy" of these ailments. Based on the observation that the causative and predominant allergenic components in the extracts comprise protein backbone structures in the molecular weight range of 10–70 kDa, it has become common practice in the manufacturing process of allergenic extracts to dialyse or ultrafilter the aqueous extracts through membranes of 10 kDa nominal cut-off in order to remove less relevant components with a molecular size lower than 10 kDa, thereby retaining the multivalent antigenic proteins in the range of 10–100 kDa in order to improve the quality of the allergenic extracts for clinical application. In some cases, a lower cut-off limit is chosen of 3 kDa or 5 kDa.

According to current theory the exposure to environmental allergens in man causes the formation of allergen-specific antibodies of the IgG- and IgE-isotypes. Within an immunological context, allergens may therefore be regarded as ordinary IgG-antibody inducing foreign antigens endowed with the ancillary property—either due to special molecular characteristics or to the simultaneous presence in allergenic extracts of appropriate modulators—to additionally promote the biosynthesis of antibodies of the IgE class. At one time, such antigens were therefore more appropriately called "atopic allergens" [1]. Genetically predisposed, so-called "atopic" human beings are particularly prone in this respect to respond with elevated levels of allergen-specific IgE antibodies. After the initial induction or "sensitization" phase, renewed contact with the allergen is considered to lead to the local formation of allergen—(IgE) antibody complexes being responsible for the ultimate disease symptoms. More particularly, it is the interaction of allergens with their specific IgE-class sessile antibodies bound to IgE-(e) receptors on cell membranes (i.e. of mast cells or basophilic leucocytes) which is thought to trigger the sequence of biochemical events eventually leading to the release of mediator substances responsible for the clinically manifest symptoms of allergy. In order to reduce the risk of anaphylactic side-reactions during immunotherapy a large number of approaches has been described. Recently, PCT/EP96/01733 was published (Nov. 7, 1996) disclosing a novel pharmaceutical composition for use in desensitization therapy of allergy sufferers. This composition comprises tyrosine and a polymerised allergen. Other approaches were presented already in the early eighties but were found inadequate. GB-A-1,492,973 describes a coprecipitate of tyrosine and an allergen that has been modified by an agent causing intramolecular crosslinking. EP-A-0.367.306 describes a process of preparing polymerised allergens also providing crosslinking and purportedly resulting in reduced allergenicity. In yet another old publication EP-B-0.038.154 which was published already in 1981 the treatment of an allergen with polysarcosine to reduce its allergenicity is described. In particular polysarcosine with a molecular weight of 2,000–12,000 is useful according to the publication. This document also refers to UK patent 1.282.163 describing an improved form of therapy wherein the allergenicity of an allergen is reduced by treatment with glutaraldehyde, which is suggested as retaining the ability to elicit blocking antibodies but exhibiting reduced allergenicity, thus rendering it more suitable for desensitization therapy. An alternative approach was provided in UK patent no 1.578.348 wherein it is stated that allergen-polyethylene glycol conjugates are capable of eliciting the desired therapeutic effect of suppressing allergen specific IgE production. These materials are stated as being non allergenic and non immunogenic. For the intended immunotherapy of allergic diseases by means of tolerogenic allergen fragments, the products of choice should be closely similar to the natural T-cell epitopes generated within so-called "antigen-presenting cells" (APCs) by acid hydrolases and other enzymes under physiological conditions. This particular approach has been taken in the prior art in U.S. Pat. No. 4,469,667 and European Patent EP 0113712 B1 (see also ref. 6 and 7). Such natural elements include possible peptide-bound haptenic chemical structures and may be imitated in the laboratory by subjecting the allergenic extract components to proteolytic cleavage under controlled conditions. One of the many routes of research in this field suggests that the treatment of allergy in man should be performed using allergen derivatives which do not induce specific IgE antibodies, i.e. allergen derivatives depleted of their so-called IgE-binding "B-cell epitopes".

Thus, a large number of different ways to provide compositions for desensitization, i.e. by reduction of allergenicity, has been suggested over the past twenty years. Considerable effort has gone into addressing the problem in various ways, so far with little result. In order to get a better understanding of the requirements for treatment, it is essential to assess what actually happens during the induction or elicitation of an allergic response.

Induction of an immune response to foreign antigens requires the cooperation of various categories of cells, i.e. in the simplest form the so-called "antigen-presenting cells" (APC) and the T- and B-lymphocyte populations. The first signal, namely between APCs and T-lymphocytes, is composed of antigenic peptide fragments which arise during the intracellular processing (by proteolytic cleavage) of a foreign antigen internalized by APCs, e.g. macrophages. The (foreign) antigenic fragments (also known as "T-cell epitopes") are subsequently recycled to the outer membranes of the APC where they then become exposed in the form of ligands associated with membrane-bound Class II antigens of the Major Histocompatibility Complex (MHC). From among the populations of T-(helper) lymphocytes (Th1-, and Th2-cells) recognizing such T-cell epitopes on APCs and cooperating by themselves with immunoglobulin-secreting B-lymphocytes, activation of the allergen-specific Th2-cell clones in particular is considered to exercise a pivotal role in the development of human atopic diseases. Unlike Th1-cells, Th2-cells activated by contact with APCs expressing the proper T-cell epitopes on their surface produce relatively large amounts of the interleukins 4 (IL-4) and 5 (IL-5), which may among others act as cytokine signals promoting IgE biosynthesis by B-lymphocytes or plasma cells. Based on this, a contemporary theory of "immediate Type I" (atopic) allergy purports that in atopic human beings a relative preponderance of Th2 over Th1 lymphocytes occurs, resulting in increased IgE synthesis, and that active therapy should therefore aim at restoring the balance of allergen-specific T-cell activity from Th2>Th1 to Th1≧Th2. Deliberate manipulation of allergen-specific T-cell clones by way of T-cell epitopes derived from allergenic molecules thereby suggests itself as a possible new approach to successful immunotherapy, with the restriction that such epitopes should not bind, nor induce allergen-specific IgE antibodies [2,3]. However, recent clinical trials with some synthetic T-cell peptide epitopes structurally defined from the amino acid sequence of selected IgE-binding antigens derived from molecular cloning and recombinant technology have so far failed to achieve the desired beneficial effects [4,5] so that this most recently taken route does not seem to lead to results.

Without wishing to be bound by theory, it seems well-established that the interaction between APCs and Th-cells requires co-stimulatory factors involving several membrane receptors. Evidence also exists that if only the first signal, i.e. T-cell epitope recognition takes place, T-cell anergy may result. After an initial phase of stimulation these Th2 cells become unresponsive to further stimulation by allergen-pulsed APCs. Hence, T-cell anergy can be induced in allergen-specific Th2 cell clones following stimulation with allergen-derived peptides. Such anergic Th-cells fail to provide help to IgE-producing B-cells, leading to down-regulation of IgE levels. There are some preliminary clinical data to support the idea that the presentation or administration of supra-optimal doses of preformed MHC-compatible T-cell epitopes can, in the absence of co-stimulatory signals and perhaps even in the pre-existing immune state, induce T-cell anergy and immunological tolerance [6,7].

Extracts of individual allergenic source materials are known to embody a large variety of distinct IgE-binding protein allergens. Furthermore, any individual protein allergen from a single source may display a range of diverse non-IgE binding T-cell epitopes. In view of the abundance of T-cell activating epitopes and the difficulty of selecting the proper tolerogenic peptides from among them, it would seem reasonable to assume that efficacious broad-spectrum immunotherapy with T-cell epitopes can best be achieved with collections of non-IgE-binding fragments of the natural library of allergens in the source material, rather than with a few selected synthetic peptides or even recombinant allergens. This becomes even more poignant in the context of the probable chemical nature of the dominant epitopes.

Current opinion which maintains that T-cell epitopes are peptides of linear amino acid sequence which may—once identified—be produced synthetically. This point of view, however, wholly negates that naturally occurring allergens most often carry post-translational side-chains composed of carbohydrates or other organic compounds conjugated chemically to the protein backbones. Such chemically conjugated structures or "haptens" often represent immunodominant sites which are retained on enzymatically produced fragments of allergens, but are absent from synthetic peptides or recombinant allergen transcripts. And, finally, allergen science and technology has remained wholly silent with respect to a most important practical issue, namely the chemical and physical interactions taking place among the multitude of components in unrefined allergenic extracts, leading to degradation products and the formation of non-physiological molecular complexes. For these reasons in combination with the lack of practical results with the compositions described above, an alternative approach was taken to develop more appropriate preparations for the treatment of allergies.

BACKGROUND OF THE INVENTION

In the foregoing it has been assumed, as is usually done, that the immune system handles allergens just the way it does ordinary foreign antigens. However, this presumption neither explains why allergens—unlike the common protein antigens—induce the formation of specific IgE-antibodies in tandem with IgG-antibodies, nor does it help to understand why only a small segment of the human population (the "atopic" people) not only produces elevated levels of such IgE-antibodies, but is also prone to develop clinically manifest allergic disease. Obviously, additional factors must be considered before designing the most suitable allergen preparations or—fragments for counterregulating the pathomechanism(s) of allergic disease. One of these factors concerns the complement system and its activation by components of allergenic extracts.

Aqueous extracts of allergenic "indoor" source materials have long been known to consume haemolytic complement (huC) in human serum in vitro [8]. Chemical studies of numerous allergenic extracts have uncovered the almost universal presence of organic decomposition products, which include >10 kDa Maillard-type reaction products of proteins or peptides with carbohydrates (i.e. melanoidins), as well as soluble (eu-)melanins in extracts of house dust and animal danders. These constituents have been shown to be responsible for complement activation and partly also for the in vivo positive skin reactions in atopic allergic subjects. On the other hand, in aqueous extracts of typical "outdoor" allergens like the plant pollens, the main agents involved in complement activation have recently been identified by the inventors to be free or protein-adsorbed condensed or hydrolysable tannins, or flavonoids and other polyphenols conjugated in high density to the protein carrier molecules in the form of haptens. The melanoidin, melanin or tannin degradation products by themselves were already described in 1983 as being non-immunogenic, although they may present themselves in physical association with the protein antigens in the extracts, thereby leading to the preferential induction of antibodies of the IgE-class [9].

The mechanism of non-antibody-mediated complement activation by these particular components of allergenic extracts involves the components C1, C4, C2, and under special conditions C3, of the classical pathway. Thus, the local activation of complement by modulating compounds in allergenic extracts may lead to the generation of the powerful histamine-liberating anaphylatoxin C3a and the fragment C3b, a key factor in the regulation of the cellular immune system. It has been demonstrated, furthermore, that complement in the serum of "atopic" individuals tends to be more sensitive to activating factors than observed with the sera of healthy control persons [8].

We have unexpectedly observed that tannins and melanoidins in allergenic extracts are capable of activating the complement system even in the absence of antigens. Hence, these agents truly exhibit adjuvant properties by generating complement factors like (multivalent) C3b which provide the appropriate "second" signals for the proliferation of B-lymphocytes and the stimulation of antibody synthesis. The incriminated C3b outer membrane receptor CD21 on B-cells by itself is a ligand for the lectin CD23 on B-lymphocytes, which in its turn has been recognized as a low-affinity IgE (Fc)-receptor. Although the details of the chain of T-cell/B-cell and complement receptor interactions are beyond the scope of this document, it seems evident that the stimuli for allergen-specific IgE antibody synthesis and for non-allergen-specific complement activation could be closely linked [10]. Since heightened anti-allergen IgE production is generally considered to trigger off the clinically manifest allergic reactions, it thus follows that complement—, CD21- and CD23-activating agents in allergenic extracts intended for immunotherapy and tolerance induction are undesirable and must be eliminated as much as possible before a successful induction of T-cell anergy can at all be attempted. Awareness of this prerequisite and its practical implementation is entirely new and unprecedented in the prior art.

The recognition of at least two functionally distinct groups of organic compounds in allergenic extracts, i.e. complement-activating tannins and melanoidins (or "adjuvants") on the one hand, acting synergistically with antigenic (glyco)protein components on the other, represents a new and unexpected breakthrough in the understanding of IgE-mediated allergic diseases in man, which has important technological repercussions for the design and production of novel medicines. It follows, for example, that for the manufacture of tolerogenic T-cell epitope compositions not leading to IgE-antibody induction, the allergenic starting material must be cleared as much as possible of complement-activating factors.

Apart from their complement-activating properties, the tannins and melanoidins exert many other undesirable effects. These compounds adsorb tightly to most proteins by multiple hydrogen-bonding and hydrophobic interactions, thereby shielding the proteins from enzymatic attack. Conversely, tannins and melanoidins inhibit a large variety of enzymes operating at neutral or slightly alkaline physiological pH-values, including the serine proteinases trypsin, chymotrypsin and kallikrein [11]. Since the physical forces involved in tannin/melanoidin-protein interaction reversibly drop to zero at pH-values below 2.5, the proteinase of choice for the enzymatic production of the T-cell epitopes from allergenic macromolecules is the gastric enzyme pepsin with its optimum activity at pH 2. At this pH-value, the tannins and melanoidins (which have a maximum molecular size of about 5 kDa) dissociate from the proteins and may be removed by dialysis or ultrafiltration. Therefore, it is absolutely vital that the enzymatic digestion process with pepsin for allergen fragmentation is preceded by a dialysis step from acid (less than pH 2.5) medium in the absence of enzyme, in order to remove interfering tannins and/or melanoidins without affecting the allergenic protein structures. If these complement-activating polyhydroxylic substances were not removed prior to the peptic digestion process, they would re-associate with the desired T-cell peptides upon neutralization and make these unavailable in the final pharmaceutical product. The candidate starting material for enzymic fragmentation can therefore comprise the "depigmented" allergens prepared at pH 2 in the absence of enzyme and described in detail in European Patent Number EP 0 662 080 B1. The tannins and/or melanoidins can be removed in a dialysis step through 5 kDa membranes.

As detailed in EP 0 662 080 B1, the depigmentation process of allergenic proteins in dilute hydrochloric or sulphuric acid solution at pH 2.0±0.1 removes a substantial proportion (15–60% by weight, depending on the source material) of the dissolved >10 kDa components in allergenic extracts by dialysis or ultrafiltration directly from the acid medium through 10 kDa cut-of membranes. The molecular size of the desorbed components therefore is in a range below 10 kDa and includes the natural tannins, (eu)melanins and melanoidins which normally have a molecular mass of around 5 kDa. If this precautionary acid dialysis step is not being taken prior to the digestion phase e.g. a digestion phase with added pepsin,—like it was not incorporated in the procedures described in U.S. Pat. No. 4,469,667 and European Patent EP 0113712 B1—neutralization of the acidic solution in the case of pepsin after hydrolysis at pH 2 will cause the re-association of tannin-peptide complexes as discussed above, thereby shielding the desired T-cell epitopes from subsequent recognition by the cellular immune system. Failure to remove the tannins and melanoidins prior to enzymatic digestion will also leave the complement-activating power of the final product unaffected and lead to unwanted stimulation of IgE synthesis upon human application.

Figure 1:
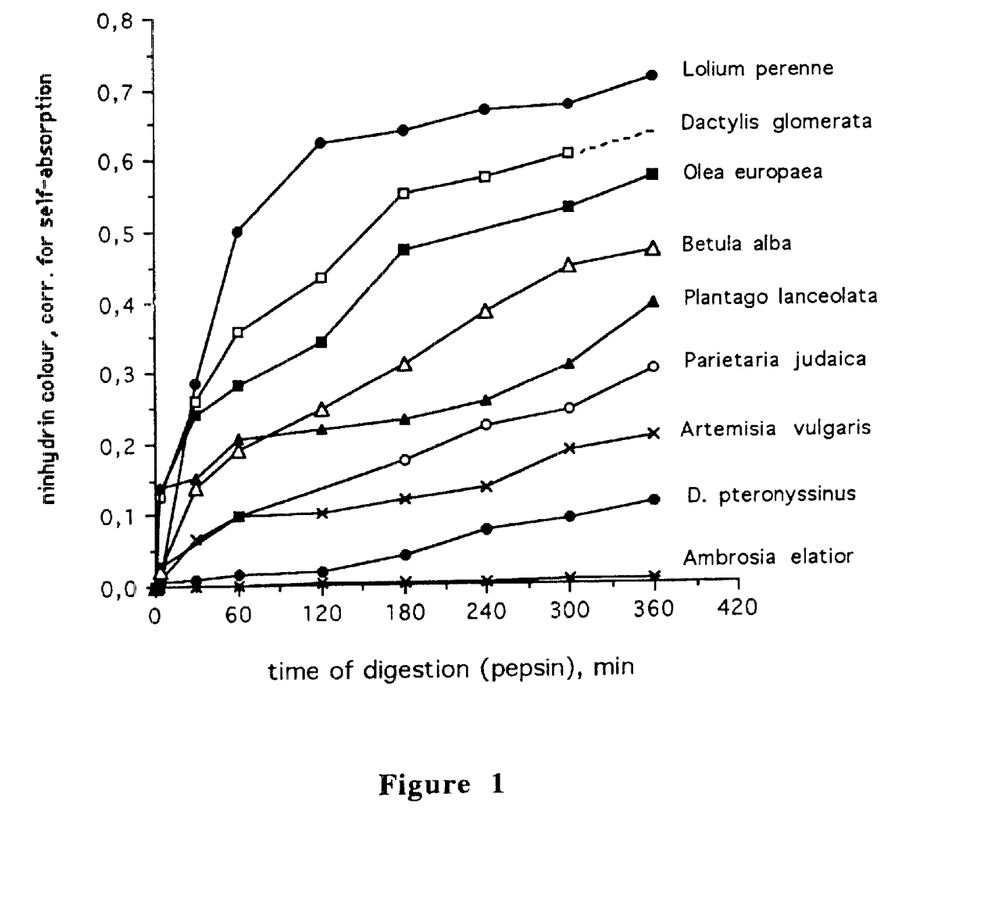

Despite a correctly executed depigmentation process, chemically bound polyphenolic and Maillard-type structures can often still be identified chemically and spectroscopically even on properly depigmented allergenic proteins [12]. Such conjugated polyphenolic and carbohydrate derivatives form an integral part of the molecular structure of the protein allergens and cannot be removed in acid medium. It has indeed been demonstrated that such non-protein side chains may, even as haptens, form part of the B-cell epitope sites recognized by specific IgE- and IgG-antibodies, as outlined in U.S. Pat. No. 5,384,395 and European Patent EP A 0,387,952. In point of fact, the elimination of physically adsorbed tannins and melanoidins by the depigmentation process of EP 0 662 080 B1 aids in unmasking these protein-conjugated haptenic structures, leading in most allergens to a slight increase in the binding of specific IgE-antibodies. On the other hand, the haptenic distribution and density on the protein antigen carrier may be such that particular >10 kDa depigmented (HMW-D) preparations cannot easily be enzymatically hydrolysed, as has been reported for the allergens from the pollen of *Parietaria judaica* [12]. In contrast to what has been implied in European Patent EP 0113712 B1, the ease of enzymatic digestion by pepsin was found to be different among distinct depigmented >10 kDa allergen preparations, meaning that the conditions of enzymatic hydrolysis must be adapted dependent on the allergen source. As shown in the examples of FIG. 1 of the subject patent application, the rate of appearance of free peptide amino groups as determined with a ninhydrin reagent during pepsin digestion indeed shows marked variation among the various allergenic pollen preparations.

Figure 2:
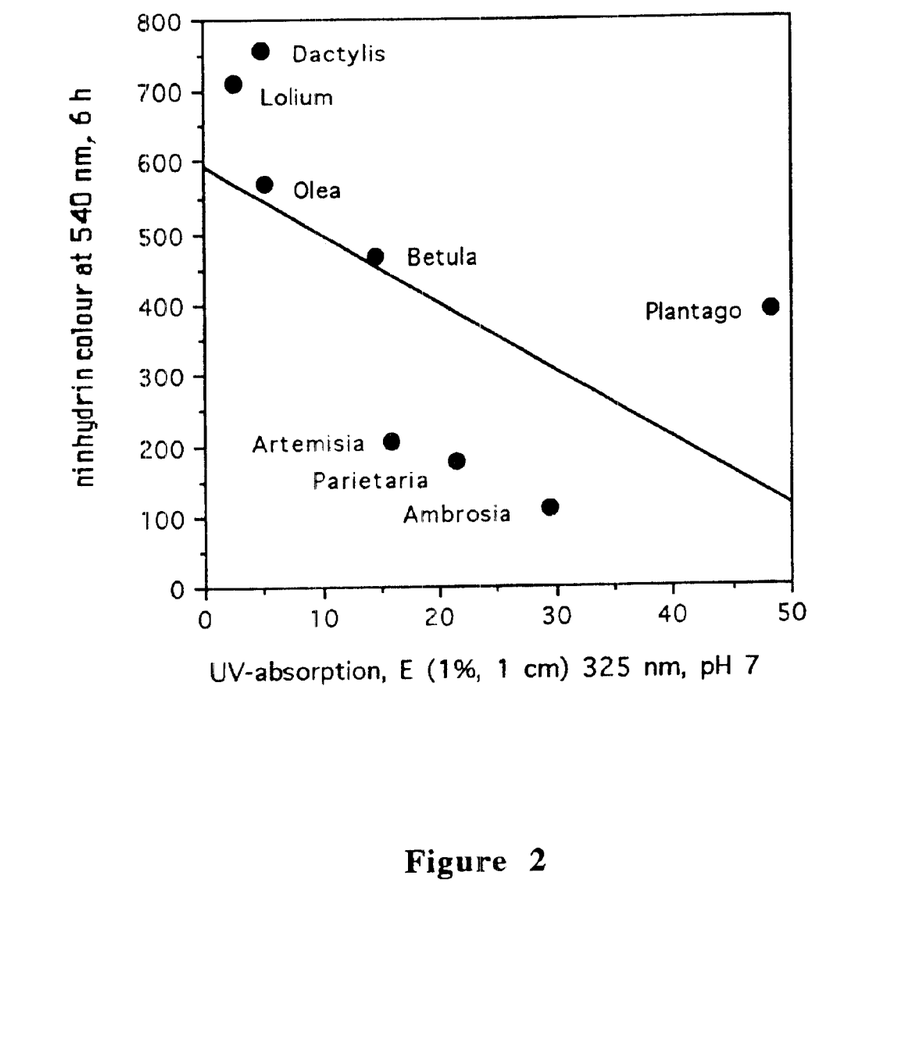

Dominant haptenic structures found incorporated on allergenic protein backbones either belong to the group of the polyhydroxylic flavonoids and other polyphenols, which under oxidative conditions form strong thioether bonds with cysteine residues in the protein macromolecule, or represent chemical rearrangement products of hexoses or pentoses linked to the e-amino groups of lysine side-chains [1]. Both the S-linked and the N(e)-linked haptenic structures absorb ultraviolet light in the range of 300–350 nm, where pure protein absorption is negligible. As illustrated with the examples of FIG. 2, an inverse relationship is indeed observed between the hapten density approximated by UV-spectroscopy and the rate of digestion of the allergenic hapten-protein complexes by pepsin, as measured in terms of liberated ninhydrin-reactive free amino groups.

In some cases of highly pepsin-resistant HMW-D preparations, it can be shown by electrophoretic methods that despite the paucity of liberated free amino groups (FIG. 1)—fragmentation is nevertheless apparent by the loss of detectable protein constituents. In the example of the Parietaria pollen, clear-cut fragmentation can also be demonstrated by the loss of complement-activating power—but not of IgE-binding—in the enzymatic (Fb-D) fragments by a factor of at least 100. In view of the strongly reducing properties of the polyphenol- or lysine-sugar structural elements, oxidation may in some cases be an essential prerequisite for fully eliminating both the IgE-binding and complement-activating sites. Oxidation of the HMW-D preparations before fragmentation can be carried out using a variety of chemical agents, e.g., with periodate salts (see below). However, in order to protect possible carbohydrate T-cell epitopes, the method of choice is oxidation by means of ultraviolet irradiation, which has been shown to diminish both the complement-activating and the IgE-binding potencies (13). In the case of the HMW-D preparations from the pollen of some weeds, trees and herbs, a supplementary oxidation step may therefore be introduced after depigmentation but before fragmentation (see below).

The enzymic fragmentation and (optional) oxidation procedures according to the invention are applicable to all known allergenic environmental, indoor and outdoor materials, including mites, insects, moulds, the pollen of the families of the grasses, weeds and trees, organic dusts in occupational environments, etc. These materials can be extracted and subjected to a depigmentation process as described, e.g., in EP 0 662 080 B1, the content of which patent is hereby incorporated by reference. The subsequent correct choice of the fragmentation conditions (pre-oxidation, ratio of enzyme to substrate, period of enzymatic hydrolysis, etc.) to obtain proteolytic degradation of the allergenic matter in the extract may depend on preliminary experimental verification due to the nature of the source material. Such choice is a matter of routine to a person skilled in the art and can be carried out without undue burden.

The proposed preparation of natural T-cell epitopes follows a series of steps which are exemplified in the procedure described in the example. In general terms the method according to the invention is a method of producing a tolerance providing extract for application to an individual in order to provide tolerance against allergenic material, said method comprising a) extraction of allergenic source material
b) removal of material with molecular weight lower than 3,5 kDa, thereby giving HMW-N fraction, optionally freeze drying HMW-N
c) removal of tannins and melanoidins that are physically attached to allergen material in HMW-N from the fraction, thereby giving depigmented HMW-D fraction free of free tannins and melanoidins and non conjugated tannins and melanoidins, optionally freeze drying HMW-D
d) degradation of protein present in HMW-D fraction thereby producing fragments with a molecular weight between 1 and 10 kDa, said product of step d) being Fb-D, the operations of steps a–d being executed in a manner known per se for said steps.

The invention also comprises an extract of allergenic source material comprising fragments of allergens retaining their natural T-lymphocyte stimulating epitopes but free of IgE-binding epitopes, maximally depleted of complement-activating agents, and safe for use as compositions for inducing a state of specific T-cell anergy and immunological tolerance in allergic human beings. The extract according to the invention can be derived from allergenic sources selected from known environmental, indoor or outdoor allergenic materials, including insects, mites, moulds, pollen of grasses, weeds, flowers, shrubs or trees, and from allergenic materials in the occupational environments.

Such an extract is preferably one wherein IgE-binding potency of the allergen fragments expressed as the quantity of freezedried material required for 50% inhibition of IgE-binding under standard assay conditions is at least 100 times lower than that of an untreated extract in the same solvent and under the same conditions. Alternatively or in combination with the above the extract according to the invention is one wherein the complement-activating potency of the allergen fragments expressed for example as the quantity of freezedried material for causing 50% loss of human haemolytic complement, is at least 100 times lower than that of an untreated extract in the same solvent and under the same conditions.

The extract according to the invention in any of the above-mentioned embodiments may be one, wherein the T-lymphocyte stimulation index of the allergen fragments is 50–150% relative to that of an untreated extract in the same solvent and under the same conditions. In particular, the extract according to the invention is one wherein the allergen fragments have a molecular weight between 1 kDa and 10 kDa, as determined by dialysis of an aqueous solution at pH 7.0 through membranes of such nominal cut-off values. The extract according to the invention is deprived of free and/or protein-adsorbed tannins, melanoidins and other pigments.

In short, a preparation obtainable according to the method of the invention as disclosed also falls within the scope of the invention. Such preparation according to the invention will suitably be in a pharmaceutically acceptable dosage form in order for application to humans and/or animals to occur.

Use of a preparation according to the invention as active component of a medicament for the treatment of an allergic individual, with the aim of inducing tolerance to the natural allergenic substance from which the preparation is derived, is also considered a suitable embodiment of the invention.

EXAMPLE ILLUSTRATING EXTRACTION, DEPIGMENTATION AND FRAGMENTATION IN A PROCESS ACCORDING TO THE INVENTION

A. Preparation of HMW-N.

Dried allergenic source materials like defatted plant pollen powders, animal danders, spent mite cultures or the dried bodies of clean mites or other insect bodies, are suspended in a solution of 0.01 M phosphate buffer pH 7.0 containing 0.15 M NaCl (PBS). Extraction is done twice with stirring in the cold room at +4° C., namely in the first run for 4 h, whereupon the residue after centrifugation is re-extracted for 18 h and centrifuged. The combined extracts are dialysed against 5 volumes of distilled water using a Pellicon® system equipped with membranes of 10 kDa nominal cut-off (ref: Millipore®, PLBC 000 05). The dialysed >10 kDa retentate is then dried by lyophilization to give the >10 kDa crude allergen product HMW-N. In selected cases, namely where "minor" allergens of less than 10 kDa are known to exist, the 10 kDa membranes may be replaced by 3.5 kDa dialysis sheets.

B. Preparation of HMW-D

The details of the depigmentation procedure have been laid down in EP 0 662 080 B1. Briefly, the freezedried HMW-N product sub A) is dissolved at room temperature in distilled water at a concentration of 10 mg/ml. To this solution is added at room temperature and with constant stirring 2 N HCl and, on approaching the end-point, 0.1 N HCl to bring the pH down to 2.0±0.1; stirring is then continued for at least 15 minutes. Chromophoric substances or "pigments" desorbed in the acidic medium from HMW-N are then eliminated by repeated dialysis or ultrafiltration in the cold room at 4° C. for at least 17 h against several changes of distilled water through 10 kDa cut-off membranes, whereby the pH of the >10 kDa retentate solution rises to a value of about 3.5. The retentate solution after exhaustive dialysis is brought to pH 7.0±0.1 by the addition of 1,0–0.1 N NaOH. The neutralized solution is finally centrifuged, passed through a 0.2 $\mu$m sterile filter and dried by lyophilization to give the depigmented allergenic product HMW-D.

C. Preparation of HMW-Dox

In a prototype procedure, a sample of lyophilized HMW-D is dissolved in 0.05 M (50 mM) sodium metaperiodate at pH 5.3 and left with stirring for 1 h at ambient temperature. The solution is then passed through a small column of Sephadex® G25 in distilled water, and the first eluate fractions coming off the column are pooled and freezedried to give the oxidized preparation HMW-Dox. The potency of the oxidized preparations is determined in comparison to the original HMW-D products by way of haemolytic complement consumption and by inhibition of specific IgE antibody-binding according to established techniques. An example for the case of HMW-D from *Parietaria judaica* pollen is given in Table I. To avoid contamination with residual chemicals or unwanted fissure products, preference should however be given to oxidation of HMW-D in aqueous solution by irradiation with ultraviolet light as described in the prior art (13).

D. Preparation of Enzymatic Fragments Fb-D

In the proposed procedure for obtaining the natural T-cell epitope peptides or hapten-peptides derived from protein digestion, the starting materials are the depigmented preparations HMW-D obtained according to the processes described sub B) and in European Patent EP 0 662 080 B1, or HMW-Dox described sub C). The procedure for obtaining the enzymatic fragments Fb-D from both starting products is identical and may be detailed as follows.

The lyophilized depigmented material HMW-D (or HMW-Dox) is dissolved in 10 volumes of bi-distilled water and brought into a double-walled vessel allowing the circulation of water at 37±1° C. through the outer and inner wall by means of a peristaltic pump during the digestion period. To this solution is added with constant stirring 2 N HCl to bring the pH down to about 2.5. The proteolytic enzyme pepsin in the immobilized form coupled to 4% crosslinked Sepharose® (Sepharose-pepsin, Sigma Chemical Co., St. Louis, USA, ref. cat. P-3286) is then added as a dry powder in a ratio of 4 units of pepsin activity per mg of HMW-D (i.e. about 1:5 enzyme/substrate w/w or otherwise, depending on the allergen source). The suspension is then adjusted to pH 2.0±0.1. by the dropwise addition of 0.1 N HCl, and stirring is continued for at least 6 hours at 37±1° C., maintaining the pH-value of the mixture at 2.0±0.1 by automatic pH-stat control. At the end of the digestion period, the mixture is neutralized to pH 7.0 with 2.0 N-0.1 N NaOH and then filtered through a 0.4 $\mu$m membrane to remove the enzyme particles. Distilled water is then added to give a final volume twice that of the original solution, followed by dialysis in a Minitan® tangential flow system equipped with a 10 kDa Millipore membrane. The outer liquid (molecular size M<10 kDa) is collected and the inner fluid containing the >10 kDa endo-fragments Fa-D is discarded. For the purpose of illustration some analytical details of the endo-fragments Fa-D >10 kDa, largely composed of heteropolysaccharides, are given in Table I of this document. The M<10 kDa material is then cycled through a further Minitan dialysis step using a 1 kDa membrane, whereby the >1 kDa retentate is retained and the outer liquid discarded. The retentate solution is finally sterile-filtered through 0.22 $\mu$m filter membranes and lyophilized to give the desired 1 kDa >Fb-D<10 kDa fragment product.

The yields and spectroscopic characteristics of the starting products HMW-N, the intermediate preparations HMW-D (or HMW-Dox), the undigested (largely >10 kDa heteropolysaccharidic) by-products Fa-D, and the desired end products Fb-D are collectively shown for a series of representative allergenic source materials in Table II.

Process Control

Progress of enzyme digestion is monitored by the liberation of free amino groups. At regular intervals during the process of enzymatic hydrolysis, 0.5 ml samples are withdrawn from the pepsin/protein mixtures, adjusted to a final concentration of 0.5 mg/ml in 4 N sodium acetate buffer pH 5.5 and then heated for 15 min at 100° C. with 50 $\mu$l of 2% ninhydrin in acetate-buffered methylcellosolve. After cooling, absorbance is read at 541 nm against a reagent blank. Representative examples of kinetic digestion curves based on the liberation of free amino groups are collectively shown in FIG. 1.

As observed in FIG. 1, the release of detectable free amino groups with some allergenic preparations may be quite low (e.g., Parietaria, Artemisia, Ambrosia). However, this need not mean that fragmentation under the influence of pepsin does not occur because, with the exception of the pollen of *Parietaria judaica* [12], the enzymic fragments Fb-D of these allergenic products have to a considerable degree lost their binding capacity for specific IgE-antibodies, i.e. their B-cell epitopes (Table II). It may be presumed that the ninhydrin reagent may sometimes become blocked by polyphenolic peptide side-chains. However, the important point in product control is that the final fragment products Fb-D must be screened for loss of IgE-binding and complement-activating potency, together with undiminished T-cell stimulating properties.

End Product Control

Binding of Allergen-Specific IgE Antibodies

The in vitro capacity of the Fb-D end products to combine with specific IgE-class antibodies is checked by way of any of the established inhibition procedures, using the sera of specifically sensitized allergic patients. The IgE-binding potency of the fragments, expressed as the quantity of dry material for causing 50% inhibition of binding under standard assay conditions, must be at least 100 times lower than that of the parent HMW-D or HMW-Dox preparation under identical conditions, i.e. a reduction equal to or less than 1% relative to the starting material before fragmentation. Some representative data obtained with non-oxidized preparations HMW-D are collectively shown in Table III.

Complement Activation

The in vitro capacity of the Fb-D end products to activate the complement system is established by haemolytic- or enzymeimmuno-assays according to published procedures (8,13). The complement-activating potency of the fragments, expressed for example as the quantity of dry material for causing 50% loss of haemolytic complement, must be at least 100 times lower than that of the parent HMW-D or HMW-Dox preparation assayed under identical conditions, i.e. a reduction equal to or less than 1% of the potency of the starting material before fragmentation.

T-Cell Stimulation

Figure 3:
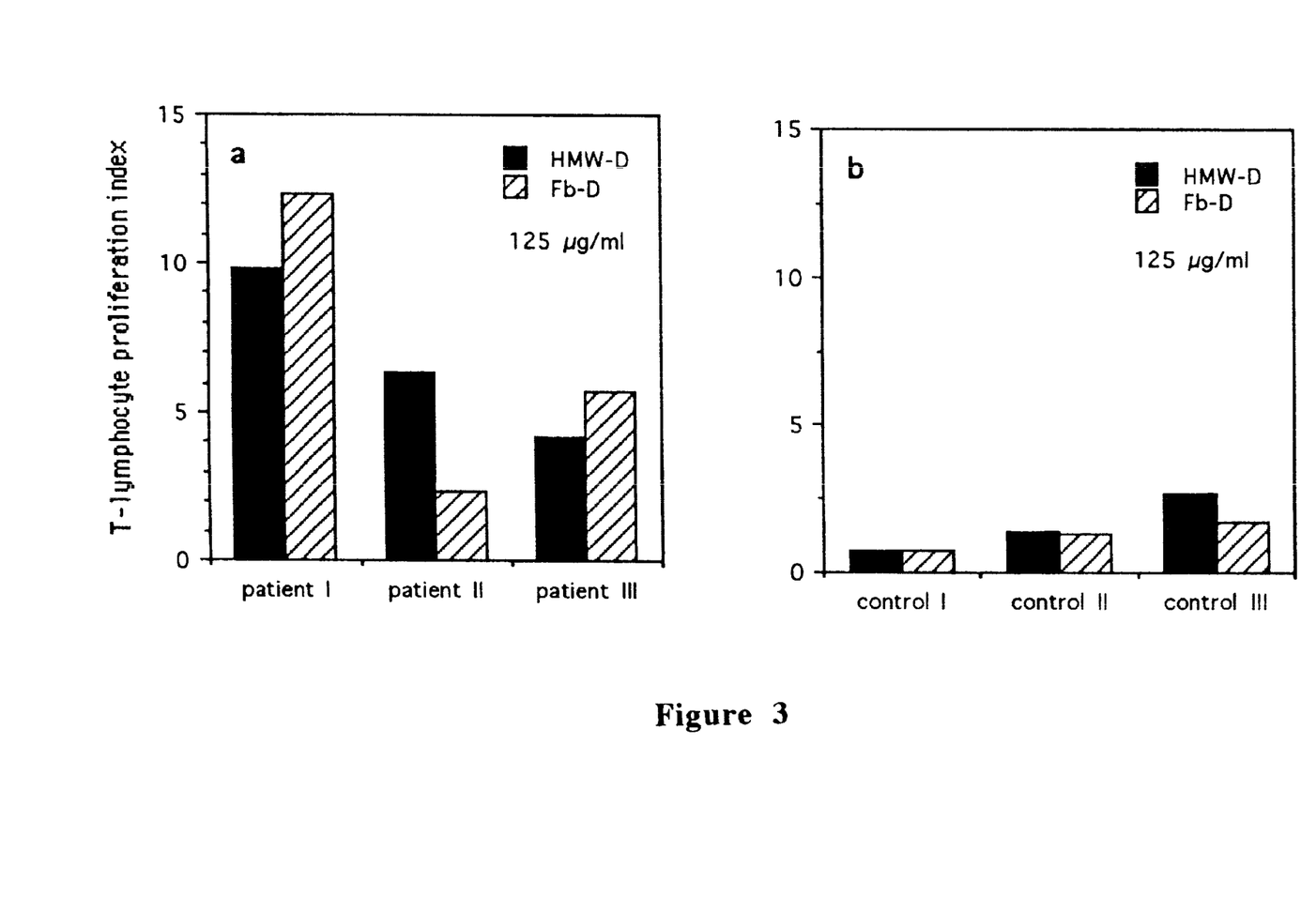

In order to verify the applicability of the end products Fb-D as viable preparations retaining the essential T-cell epitopes, the Fb-D fragments are examined for their capability to induce proliferation of T-lymphocytes isolated from the blood of specifically allergic patients according to established immunological procedures. The T-cell stimulation index of the final fragments should lie between 50–150% relative to the parent HMW-D preparation. FIG. 3 summarizes some representative data relating to the peptic fragments Fb-D obtained by fragmentation of a HMW-D preparation isolated from cultures of the highly allergenic tropical mite *Blomia tropicalis.*

Miscellaneous Methodologies

All end products Fb-D are routinely subjected to additional control procedures, for example by isoelectric focusing in polyacrylamide gel in the presence of Ampholines® in the range of pH 3–10, which—in contrast to the HMW-D parent preparations—do not reveal any constituent bands detectable with the customary protein stains. Electrophoretic separation in polyacrylamide gels using sodium dodecylsulphate (SDS-PAGE) in the presence of tricine (N-2-hydroxy-1.1.-bis [hydroxymethylethyl]glycine) unveils distribution patterns of Coomassie Blue stainable bands which are entirely dissimilar from those observed with the parent HMW-D preparations, and which may be used to verify the reproducibility of the production process.

A listing of analytical data for some representative allergenic preparations is given in Tables II and III.

DOCUMENTATION

Patents

Primary-toxic compounds or allergens, which may be isolated from plant material as well as methods for their preparation and application.

Inventor: Berrens, L. European Patent Number A 0,387, 952.

Granted 1995.

Method for the isolation of primary-toxic compounds or allergens from plant material.

Inventor: Berrens, L. U.S. Pat. No. 5,384,395. Date of Patent: Jan. 24, 1995

A process for the purification of aqueous extracts containing allergenically active proteins, extracts obtainable according to this process as well as their use.

Inventor: Berrens L. European Patent Number EP 0 662 080 B1, date of grant: Feb. 5, 1997. Date of filing: Sep. 21, 1992.

Polypeptide active pollen immunosuppressant fraction.

Michael J G, Pesce A J (Inventors). U.S. Pat. No. 4,338, 297, dated Jul. 6, 1982. Date of filing Apr. 14, 1980.

Polypeptide active pollen immunosuppressant fraction. Michael J G, Pesce A J (inventors). European Patent EP 0113712 B1, based on International application number PCT/US82/00886, date of filing Jun. 30, 1982, date of publication of patent specification Mar. 15, 1989.

Literature References

[1] Berrens L. The Chemistry of Atopic Allergens. Monographs in Allergy, Vol. 7 (Karger, Basel 1971).

[2] Shakib F (Ed). Immunological Intervention Strategies in Allergy. Biochem Soc Trans 1997; 25:383–403.

[3] Van Neerven R J J, Ebner C, Yssel H, Kapsenberg M L, Lamb J R. T-cell responses to allergens: epitope-specificity and clinical relevance. Immunology Today 1996; 17:526–32.

[4] Simons F E R, Imada M, Li Y, Watson W T A, HayGlass K T. Fel d 1 peptides: Effect on skin tests and cytokine synthesis in cat-allergic human subjects. Int Immunology 1996; 8:1937–45.

[5] Nicodemus C, Philip G, Jones N, Hirani S, Norman P. Integrated clinical experience with tolerogenic peptides. Int Arch Allergy Immunol 1997; 113:326–8.

[6] Litwin A, Pesce A, Michael J G. Regulation of the immune response to allergens by immunosuppressive allergenic fragments. I. Peptide fragments of honeybee venom phospholipase A2. Int Arch Allergy Appl Immunol 1988; 87:361–6.

[7] Litwin A, Pesce A J, Fischer T, Michael M, Michael J G. Regulation of the human immune response to ragweed pollen by immunotherapy. A controlled trial comparing the effect of immunosuppressive peptic fragments of short ragweed with standard treatment. Clin Exp Allergy 1991; 21:457–65.

[8] Berrens L. The Atopen: A Rehabilitation. Ann Allergy 1976; 36:351–61.

[9] Francus T G, Siskind G W, Becker C G. Role of antigen structure in the regulation of IgE isotype expression. Proc Natl Acad Sci USA 1983; 80:3430–4.

[10] Sutton B J, Gould H J. The human IgE network. Nature 1993; 366: 421–8.

[11] Berrens L. Digestion of atopic allergens with trypsin, α-hymotrypsin and pancreatic kallikrein, and influence of the allergens upon the proteolytic and esterolytic activity of these enzymes. Immunochemistry 1968; 5:585–605.

[12] Gonzalez Romano M L, Gallego M T, Berrens L. Extraordinary stability of IgE-binding Parietaria pollen allergens in relation to chemically bound flavonoids. Mol Immunol 1996; 33: 1287–93.

[13] Berrens L, Hënocq E, Radermecker M. Photoinactivated allergens. I. Preparation, physicochemical and biological properties. Clin Allergy 1973; 3:449–59.

TABLE I

Effect of oxidation with sodium meta-periodate on the IgE-binding and complement-activating potencies of depigmented allergenic preparations HMW-D from the pollen of *Parietaria judaica*.

| Product | μg in assay for 50% haemolysis | reduction factor |
|---|---|---|
| HMW-D | 0.49 | |
| HMW-Dox | 12.36 | 25.2 |

| Product | μg in test for 50% inh. IgE-binding | reduction factor |
|---|---|---|
| HMW-D | 1.5 | |
| HMW-Dox | 4.12 | 2.7 |

TABLE II

Analyses of peptic allergen fragments

| Allergen source | Fraction (*) | Yield from dry pollen/ culture, % w/w | 50% IgE-inh. (discs) μg in test | 50% IgE-inh. (EIA) μg in test |
|---|---|---|---|---|
| Ambrosia elatior | HMW-N | 15.03 | n.d. | n.d. |
| | HMW-D | 8.59 | 72.04 | 0.2 |
| | Fa-D | 4.52 | 1312.06 | no inhibition |
| | Fb-D | 0.75 | no inhibition | no inhibition |
| Betula alba | HMW_N | 2.67 | n.d. | 0.009 |
| | HMW-D | 1.72 | n.d. | 0.011 |
| | Fa-D | 0.87 | n.d. | 0.442 |
| | Fb-D | 0.42 | n.d. | 3.162 |
| Lolium perenne | HMW-N | 8.88 | n.d. | 0.081 |
| | HMW-D | 5.07 | 0.81 | 0.012 |
| | Fa-D | 2.50 | 324.00 | 5.51 |
| | Fb-D | 1.20 | 854.00 | 138.70 |
| Olea europaea | HMW_N | 8.20 | n.d. | n.d. |
| | HMW-D | 5.15 | 11.08 | 0.011 |
| | Fa-D | 1.70 | 141.30 | 2.54 |
| | Fb-D | 0.80 | 1077.00 | 17.61 |
| Parietaria judaica | HMW_N | 3.60 | 5.18 | 0.008 |
| | HMW-D | 1.85 | 3.82 | 0.0126 |
| | Fa-D | 0.93 | 3.77 | 0.012 |
| | Fb-D | 0.14 | 4.17 | 0.0102 |
| D. peronyssinus | HMW-N | 14.96 | n.d. | n.d. |
| | HMW-D | 14.51 | 2.84 | n.d. |
| | Fa-D | 6.08 | 52.70 | n.d. |
| | Fb-D | 2.59 | 452.20 | n.d. |
| Blomia tropicalis | HMW_N | 9.60 | n.d. | 0.0143 |
| | HMW-D | 5.70 | n.d. | 0.0072 |
| | Fa-D | 3.40 | n.d. | 0.0085 |
| | Fb-D | 1.20 | n.d. | 2.667 |

| Allergen source | E(1%, 1 cm) (270 nm) pH 7.4 | E(1%, 1 cm) (325–350 nm) pH 7 | ninhydrin-positive material as % equiv. glycine | % carbohydrate anthron method as % galactose |
|---|---|---|---|---|
| Ambrosia elatior | 58.64 | 38.24 | n.d. | n.d. |
| | 50.80 | 38.68 | 1.96 | 41.13 |
| | 0.40 | 1.24 | 1.58 | 36.08 |
| | 39.48 | 27.08 | 3.92 | 28.45 |
| Betula alba | 10.56 | — | n.d. | n.d. |
| | 6.92 | — | n.d. | n.d. |
| | 5.13 | — | n.d. | n.d. |
| | 6.83 | — | n.d. | n.d. |
| Lolium perenne | 7.33 | 2.82 | n.d. | n.d. |
| | 7.95 | 2.90 | 3.70 | 35.41 |
| | 1.87 | 0.73 | 2.67 | 56.48 |
| | 7.59 | 1.63 | 7.70 | 8.25 |
| Olea europaea | 51.04 | 29.02 | n.d. | n.d. |
| | 24.16 | 10.82 | 4.37 | 25.37 |
| | 11.14 | 5.62 | 2.97 | 42.09 |
| | 11.84 | 4.90 | 7.89 | 8.47 |
| Parietaria judaica | 76.20 | 41.68 | 5.44 | n.d. |
| | 40.64 | 18.92 | 3.35 | 30.07 |
| | 30.72 | 15.29 | 3.18 | 30.35 |
| | 38.88 | 24.00 | 4.09 | 38.83 |
| D. peronyssinus | 11.14 | n.d. | n.d. | n.d. |
| | 10.08 | n.d. | 3.10 | 39.78 |
| | 10.70 | n.d. | 1.69 | 64.60 |
| | 8.55 | n.d. | 2.02 | 20.27 |
| Blomia tropicalis | 26.22 | n.d. | 100.00 | 16.53 |
| | 25.42 | n.d. | 81.00 | 22.49 |
| | 30.16 | n.d. | 70.00 | 24.07 |
| | 17.12 | n.d. | 100.00 | 18.54 |

(*)The Fa-D fractions comprise the undigestible > 10 · kDa residues. The Fb-D fragments of 1 kDa < M < 10 kDa comprise the desired final products

TABLE III

Reduction factors for IgE-binding potency (reactivity with B-cell epitopes) determined by inhibition of IgE binding from specific human sera for the individual allergen products to HMW-D* conjugated chemically with cyanogen bromide to paper discs ("RAST-inhibition"). Recalculated for relative potency of HMW-D = 1.

| | Fraction | | |
|---|---|---|---|
| Allergen Source | HWM-D > 10 kDa | FaD > 10 kDa | 1 kDa < FbD < 10 kD |
| *Ambrosia elatior* | 1 | 18 | 1500 |
| *Betula alba* | 1 | 169 | 1123 |
| *Lolium perenne* | 1 | 400 | 1054 |
| *Olea europaea* | 1 | 13 | 97 |
| *Artemisia vulgaris*** | 1 | 8 | 61 |
| *Parietaria judaica* | 1 | 1 | 1 |
| *D. pteronyssinus* | 1 | 19 | 159 |
| *Blomia tropicalis*** | 1 | 1 | 370 |

*non-oxidized depigmented preparations
**reduction factors calculated from enzyme immuno assays in microtiter plates, with HMW-D coated to the surface of the wells.

LEGENDS TO THE FIGURES

FIG. 1: Kinetics of the release of ninhydrin-reactive free amino groups from a representative series of HMW-D allergenic preparations hydrolysed enzymatically by pepsin. Conditions: see text.

FIG. 2: Reverse relationship between digestibility of HMW-D preparations of pollen by pepsin (i.e. ninhydrin colour after 6 h of hydrolysis at 37° C. and pH 2), and the extinction coefficients E(1%, 1 cm) at 325 nm taken from the ultraviolet spectra in 0.01 M phosphate buffer pH 7.0.

FIG. 3: Proliferation of T-cells in cultures of peripheral lymphocytes (incorporation of radioactive thymidin, relative units) from the blood of (a) specifically allergic patients and (b) skin-test negative healthy controls upon stimulation by the depigmented preparation HMW-D and the fragments Fb-D prepared from extracts of *Blomia tropicalis.*

What is claimed is:

1. A preparation for inducing tolerance in an individual, said preparation comprising depigmented and oxidized proteinaceous components from allergenic source material, and wherein the proteinaceous components have a molecular weight in the range of 1–10 kDa, said preparation being obtainable according to the method of (a) dissolving proteinaceous components from an allergenic source material aqueous solution;

(b) separation of the dissolved proteinaceous components from the allergenic source material;
(c) removal of material with a molecular weight lower than 3.5 kDa from the dissolved proteinaceous components to provide a HMW-N fraction;
(d) depigmentation of the HMW-N fraction to provide a HMW-D fraction;
(e) oxidation of the HMW-D fraction by an oxidizing agent, ultraviolet irradiation or a combination of both, to provide a HMW-Dox fraction;
(f) digestion of the HMW-Dox fraction with a proteolytic enzyme until the majority of the proteinaceous components in the HMW-Dox have a molecular weight between 1 and 10 kDa, and
(g) recovery of the proteinaceous components with a molecular weight between 1 and 10 kDa and formulation into a preparation for inducing tolerance in an individual.

* * * * *